US00PP37198P2

(12) United States Plant Patent
Graff

(10) Patent No.: US PP37,198 P2
(45) Date of Patent: Jan. 6, 2026

(54) ***MANDEVILLA* PLANT NAMED 'QD-80'**

(50) Latin Name: *Mandevilla sanderi*
Varietal Denomination: QD-80

(71) Applicant: Poul Graff, Sabro (DK)

(72) Inventor: Poul Graff, Sabro (DK)

(73) Assignee: GRAFF BREEDING A/S, Sabro (DK)

( * ) Notice: Subject to any disclaimer, the term of this patent is extended or adjusted under 35 U.S.C. 154(b) by 0 days.

(21) Appl. No.: 19/240,782

(22) Filed: Jun. 17, 2025

(51) Int. Cl.
*A01H 5/02* (2018.01)

(52) U.S. Cl.
USPC ..... Plt./232

(58) Field of Classification Search
USPC ..... Plt./232

CPC . A01H 5/02; A01H 5/00; A01H 6/088; A01H 6/08

See application file for complete search history.

(56) References Cited

U.S. PATENT DOCUMENTS

PP32,469 P2 * 11/2020 Graff ..... A01H 6/088 Plt./232

* cited by examiner

*Primary Examiner* — June Hwu
(74) *Attorney, Agent, or Firm* — C. Anne Whealy

(57) ABSTRACT

A new and distinct cultivar of *Mandevilla* plant named 'QD-80', characterized by its compact and broadly upright plant habit; freely branching habit; dense and bushy appearance; dark green-colored leaves; freely flowering habit; and bright purplish red-colored flowers that are held beyond the foliar plane.

3 Drawing Sheets

Figure 1:
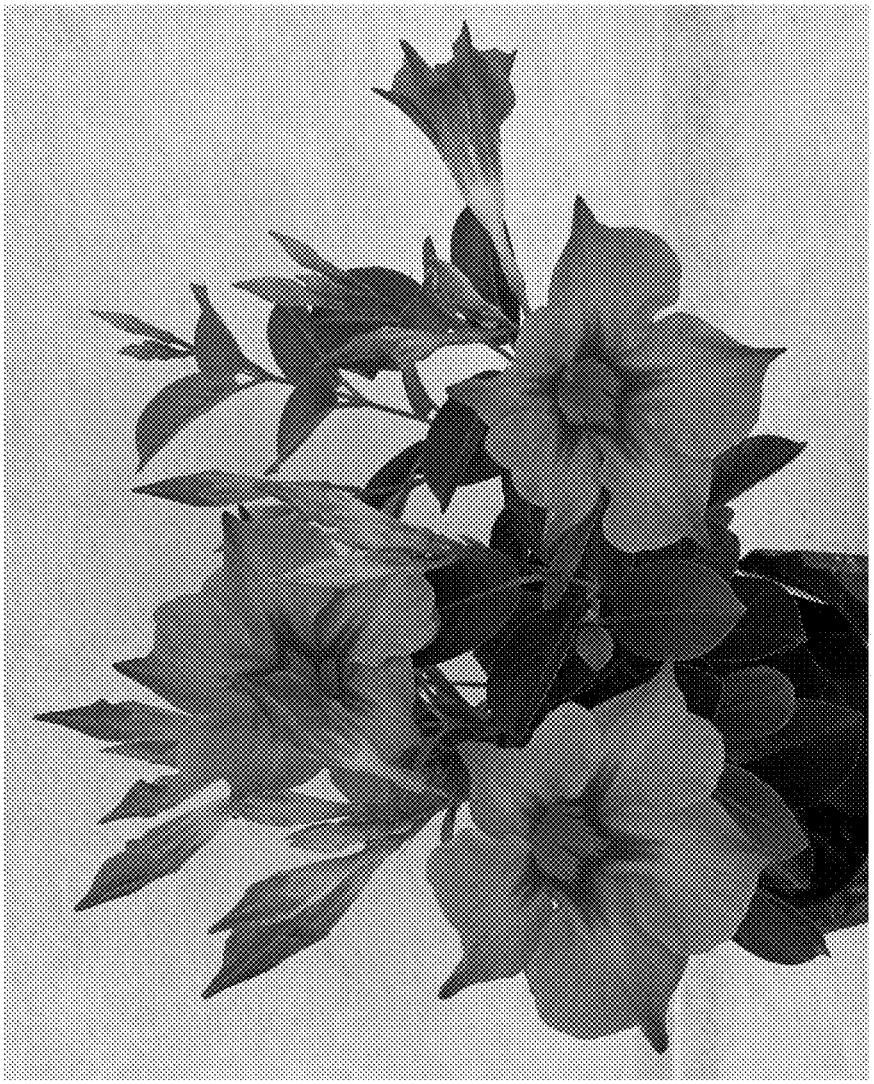

Botanical designation: *Mandevilla sanderi.*
Cultivar denomination: 'QD-80'.

CROSS-REFERENCED TO CLOSELY-RELATED APPLICATION

A European Community Plant Breeder's Rights application for the instant plant was filed by the Assignee of the instant application, Graff Breeding A/S of Sabro, Denmark on Apr. 16, 2025, application number 2359471. Foreign priority is not claimed to this European Plant Breeder's Rights application.

BACKGROUND OF THE INVENTION

The present invention relates to a new and distinct cultivar of *Mandevilla* plant, botanically known as *Mandevilla sanderi* and hereinafter referred to by the name 'QD-80'.

The new *Mandevilla* plant is a product of a planned breeding program conducted by the Inventor in Sabro, Denmark. The objective of the breeding program is to create new compact and freely branching *Mandevilla* plants with numerous attractive flowers.

The new *Mandevilla* plant originated from a cross-pollination in Sabro, Denmark in August 2016 of *Mandevilla sanderi* 'QD8', disclosed in U.S. Plant Pat. No. 32,505, as the female, or seed, parent with a proprietary selection of *Mandevilla sanderi* identified as code number M-2012-2903, not patented, as the male, or pollen, parent. The new *Mandevilla* plant was discovered and selected by the Inventor as a single flowering plant from within the progeny of the stated cross-pollination in a controlled greenhouse environment in Sabro, Denmark in May 2017.

Asexual reproduction of the new *Mandevilla* plant by cuttings in a controlled greenhouse environment in Sabro, Denmark, since September 2017 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'QD-80'. These characteristics in combination distinguish 'QD-80' as a new and distinct *Mandevilla* plant:

1. Compact and broadly upright plant habit.
2. Freely branching habit; dense and bushy appearance.
3. Dark green-colored leaves.
4. Freely flowering habit.
5. Bright purplish red-colored flowers that are held beyond the foliar plane.

Plants of the new *Mandevilla* can be compared to plants of the female parent, 'QD8'. Plants of the new *Mandevilla* differ primarily from plants of 'QD8' in flower color as plants of the new *Mandevilla* have bright purplish red-colored flowers whereas plants of 'QD8' have red-colored flowers. In addition, flower petals of plants of the new *Mandevilla* are not imbricate whereas flower petals of plants of 'QD8' are slightly imbricate.

Plants of the new *Mandevilla* can be compared to plants of the male parent selection. Plants of the new *Mandevilla* differ primarily from plants of the male parent selection in flower color as plants of the new *Mandevilla* have bright purplish red-colored flowers whereas plants of the male parent selection have red-colored flowers.

Plants of the new *Mandevilla* can also be compared to plants of *Mandevilla hybrida* 'QD5', disclosed in U.S. Plant Pat. No. 32,469. In side-by-side comparisons, plants of the new *Mandevilla* differ primarily from plants of 'QD5' in the following characteristics:

1. Plants of the new *Mandevilla* have glossier leaves than plants of 'QD5'.
2. Plants of the new *Mandevilla* have larger flowers than plants of 'QD5'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'QD-80' grown in a container.

Figure 2:
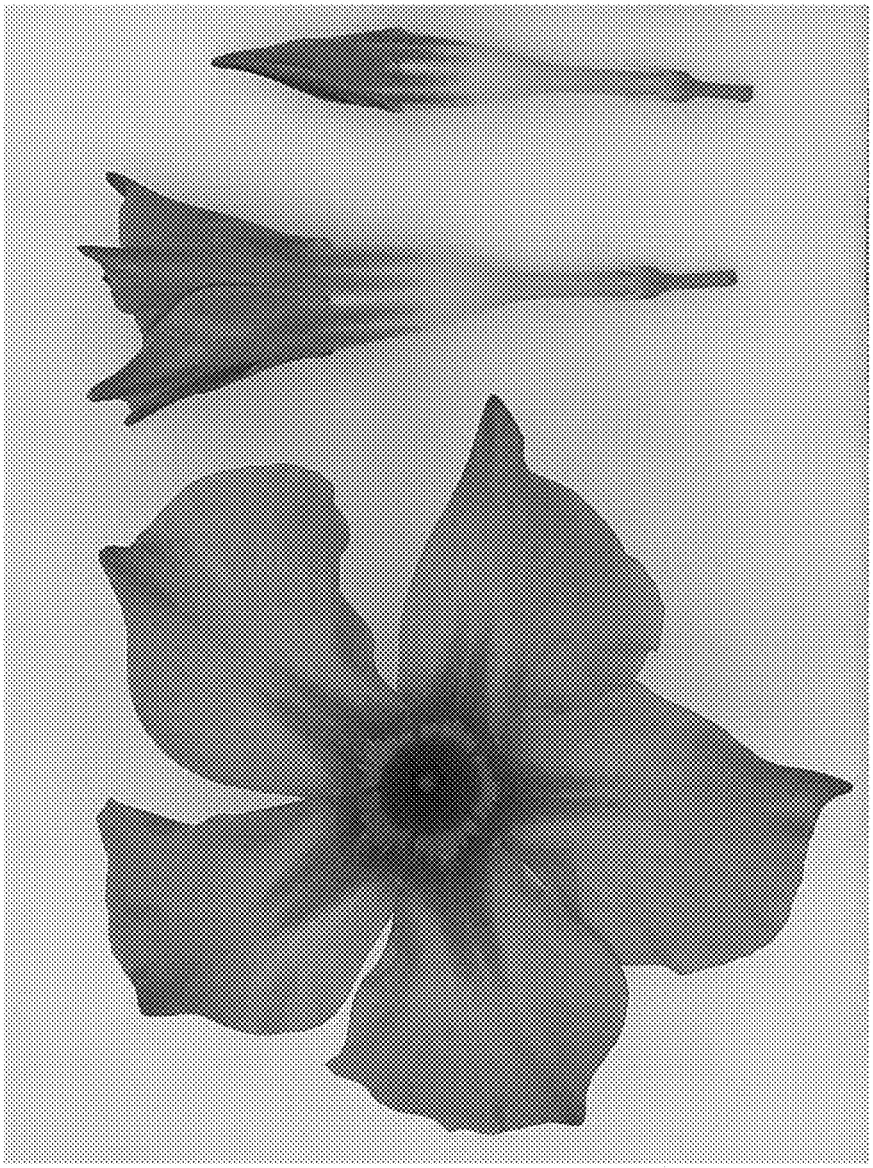

The photograph on the second sheet (FIG. 2) is a close up view of a typical open flower and developing flower buds of 'QD-80'.

Figure 3:
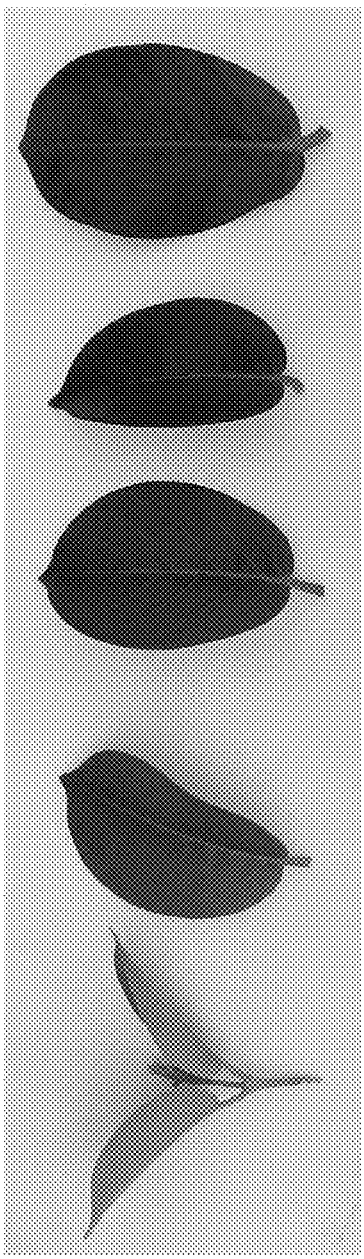

The photograph on the third sheet (FIG. 3) is a close up view of typical developing and fully developed leaves of 'QD-80'.

DETAILED BOTANICAL DESCRIPTION

The aforementioned photographs and following observations, measurements and values describe plants grown during the summer in 13-cm containers in a glass-covered greenhouse in Sabro, Denmark and under cultural practices typical of commercial *Mandevilla* production. During the production of the plants, day temperatures ranged from 20° C. to 25° C., night temperatures ranged from 19° C. to 21° C. and light levels ranged from 40 klux to 50 klux. Plants were pinched two times and were 31 weeks old when the photographs and description were taken. In the following description, color references are made to The Royal Horticultural Society Colour Chart, 2001 Edition, except where general terms of ordinary dictionary significance are used.

Botanical classification: *Mandevilla sanderi* 'QD-80'.

Parentage:

*Female, or seed, parent.*—*Mandevilla sanderi* 'QD8', disclosed in U.S. Plant Pat. No. 32,505.

*Male, or pollen, parent.*—Proprietary selection of *Mandevilla sanderi* identified as code number M-2012-2903, not patented.

Propagation:

*Type.*—By vegetative cuttings.

*Time to initiate roots, summer.*—About three weeks at soil and ambient temperatures about 21° C.

*Time to initiate roots, winter.*—About weeks at soil and ambient temperatures about 21° C.

*Time to produce a rooted young plant, summer.*—About seven weeks at soil and ambient temperatures about 21° C.

*Time to produce a rooted young plant, winter.*—About eight weeks at soil and ambient temperatures about 21° C.

*Root description.*—Fine, fibrous; typically close to 161C in color, actual color of the roots is dependent on substrate composition, water quality, fertilizers, substrate temperature and physiological age of roots.

*Rooting habit.*—Freely branching; dense.

*Tubers.*—Tuber formation has been observed on plants older than one year.

Plant description:

*Plant and growth habit.*—Compact and broadly upright plant habit; overall plant shape is broadly obovate; relatively moderately vigorous growth habit and moderate growth rate; freely branching habit; dense and bushy appearance.

*Plant height, soil level to top of foliar plane.*—About 20 cm to 25 cm.

*Plant height, soil level to top of floral plane.*—About 25 cm to 30 cm.

*Plant diameter (spread).*—About 25 cm to 30 cm.

*Lateral branch description.*—Branching habit: Freely branching habit, about two to four primary lateral branches each with typically one to three secondary lateral branches developing per plant. Length: About 10 cm to 20 cm. Diameter: About 5 mm. Internode length: About 2 cm to 4 cm. Aspect: Upright to outwardly. Strength: Strong. Texture and luster: Smooth, glabrous; semi-glossy; becoming woody with development. Color, developing: Close to 144A. Color, developed: Close to 144A; when woody, becoming closer to 199B.

Leaf description:

*Arrangement.*—Opposite, decussate; simple.

*Length.*—About 4 cm to 6 cm.

*Width.*—About 3 cm to 5 cm.

*Shape.*—Elliptic.

*Apex.*—Acuminate.

*Base.*—Rounded to cordate.

*Margin.*—Entire.

*Texture and luster, upper and lower surfaces.*—Smooth, glabrous; coriaceous; glossy.

*Venation pattern.*—Pinnate.

*Color.*—Developing leaves, upper surface: Close to 137A. Developing leaves, lower surface: Close to 146B. Full expanded leaves, upper surface: Close to 139A; venation, close to 137C. Fully expanded leaves, lower surface: Close to 147B; venation, close to 137A.

*Petioles.*—Length: About 5 mm. Diameter: About 2 mm to 3 mm. Strength: Moderately strong to strong. Texture and luster, upper and lower surfaces: Smooth, glabrous; semi-glossy. Color, upper surface: Close to 144A. Color, lower surface: Close to 143C.

Flower description:

*Flower type and flowering habit.*—Single salverform flowers arranged singly or in terminal or axillary racemes; flowers rounded star-shaped and face upright to outwardly; freely flowering habit with about two to five flower buds and about one to two open flowers per inflorescence; about 20 to 25 flowers develop during the flowering season.

*Natural flowering season.*—Plants flower continuously from spring into the autumn in Denmark; plants begin flowering about nine to twelve weeks after the final pinch.

*Flower longevity on the plant.*—About 8 to 14 days; flowers persistent.

*Fragrance*.—None detected.

*Inflorescence height* (*before flowers open*).—About 7 cm to 9 cm.

*Inflorescence diameter* (*before flowers open*).—About 6 cm to 8 cm.

*Flower buds*.—Length: About 6 cm. Diameter: About 1 cm to 1.5 cm. Shape: Rhomboidal. Texture and luster: Smooth, glabrous; slightly glossy. Color: Close to 54A and 145C.

*Flowers*.—Appearance: Flared trumpet, petals fused and five-parted; petals slightly imbricate. Diameter: About 11 cm. Depth (length): About 3 cm to 4 cm. Throat diameter: About 2 cm. Tube length: About 1.5 cm. Tube diameter: About 5 mm.

*Petals*.—Quantity and arrangement: Five petals arranged in a single whorl; proximally, petals are fused into a funnelform tube. Petal length: About 5 cm. Petal width: About 4 cm. Petal shape and appearance: Unequal spatulate to fan- shaped. Petal apex: Acuminate to acute. Petal margin: Entire; not undulate. Petal texture and luster, upper and lower surfaces: Smooth, glabrous; velvety; matte. Throat texture: Smooth, glabrous; velvety; matte. Tube texture: Smooth, glabrous; matte. Color: Petal, when opening, upper surface: Close to 67B; towards the base, close to 60B. Petal, when opening, lower surface: Close to 67A; towards the base, close to 155C. Petal, fully opened, upper surface: Close to 67B; towards the base, close to 60B; main color becoming closer to 67C with subsequent development. Petal, fully opened, lower surface: Close to 67C; towards the base, close to 155C; color does not change with subsequent development. Throat: Close to N25A; venation, close to N25A. Tube: Close to 145A; venation, close to 145A.

*Sepals*.—Quantity and arrangement: Five sepals arranged in a single whorl. Sepal length: About 1 cm. Sepal width: About 3 mm to 4 mm. Sepal shape: Lanceolate. Sepal apex: Acuminate. Sepal base: Rounded. Sepal margin: Entire. Sepal texture and luster, upper and lower surfaces: Smooth, glabrous; semi-glossy. Sepal color: When opening, upper and lower surfaces: Close to 144A; at the apex, close to 145B. Fully opened, upper and lower surfaces: Close to 144A; at the apex, close to 145B.

*Peduncles*.—Length: About 4 cm. Diameter: About 2 mm to 3 mm. Strength: Strong. Aspect: Mostly upright. Texture and luster: Smooth, glabrous; semi-glossy. Color: Close to 143A.

*Pedicels*.—Length: About 1.5 cm. Diameter: About 3 mm. Strength: Strong. Texture and luster: Smooth, glabrous; semi-glossy. Color: Close to 144A.

*Reproductive organs*.—Stamens: Quantity and arrangement: Typically five; basifixed; anthers connivent. Filament length: About 5 mm. Filament color: Close to 4D. Anther size: About 2 mm by 10 mm. Anther shape: Linear. Anther color: Close to 162C. Pollen amount: Moderate to scarce. Pollen color: Close to 162C. Pistils: Quantity: Typically one. Pistil length: About 2.5 cm. Style length: About 2 cm. Style color: Close to 144A. Stigma diameter: About 2 mm. Stigma shape: Rounded to deltoid. Stigma color: Close to 144A. Ovary color: Close to 145A.

*Fruits and seeds*.—To date, fruit and seed development has not been observed on plants of the new *Mandevilla*.

Pathogen & pest resistance: To date, plants of the new *Mandevilla* have not been observed to be resistant to pathogens and pests common to *Mandevilla* plants.

Temperature tolerance: Plants of the new *Mandevilla* have been observed to tolerate temperatures of about 10° C. to 44° C. and to be suitable for USDA Hardiness Zones 10B through 13.

It is claimed:

1. A new and distinct *Mandevilla* plant named 'QD-80' as herein illustrated and described.

* * * * *